US00PP31555P2

(12) United States Plant Patent
Magee

(10) Patent No.: US PP31,555 P2
(45) Date of Patent: Mar. 17, 2020

(54) CRAPEMYRTLE PLANT NAMED 'JM3'

(50) Latin Name: *Lagerstroemia indica*
Varietal Denomination: JM3

(71) Applicant: Jack Mitchell Magee, Poplarville, MS (US)

(72) Inventor: Jack Mitchell Magee, Poplarville, MS (US)

(73) Assignees: Greenleaf Nursery Company, Park Hill, OK (US); Evergreen Nursery, Poplarville, MS (US)

( * ) Notice: Subject to any disclaimer, the term of this patent is extended or adjusted under 35 U.S.C. 154(b) by 0 days.

(21) Appl. No.: 16/350,180

(22) Filed: Oct. 10, 2018

(51) Int. Cl.
*A01H 5/00* (2018.01)

(52) U.S. Cl.
USPC ..... Plt./252

(58) Field of Classification Search
USPC ..... Plt./252
CPC ..... A01H 5/00
See application file for complete search history.

*Primary Examiner* — Annette H Para
(74) *Attorney, Agent, or Firm* — C. A. Whealy

(57) ABSTRACT

A new and distinct cultivar of Crapemyrtle plant named 'JM3', characterized by its upright to slightly outwardly spreading plant habit; freely branching habit; vigorous and sturdy growth habit; dark greyed purple-colored leaves; numerous inflorescences with light purple-colored flowers; and good garden performance and pathogen resistance.

2 Drawing Sheets

Botanical designation: *Lagerstroemia indica* 'JM3'.
Cultivar denomination: 'JM3'.

CROSS-REFERENCED TO CLOSELY-RELATED APPLICATIONS

Title: Crapemyrtle Plant Named 'JM1'
Applicant: Jack Mitchell Magee
U.S. Plant patent application Ser. No. 16/350,178
Title: Crapemyrtle Plant Named 'JM4'
Applicant: Jack Mitchell Magee
U.S. Plant patent application Ser. No. 16/350,179
Title: Crapemyrtle Plant Named 'JM5'
Applicant: Jack Mitchell Magee
U.S. Plant patent application Ser. No. 16/350,175

BACKGROUND OF THE INVENTION

The present invention relates to a new and distinct cultivar of Crapemyrtle plant, botanically known as *Lagerstroemia indica* 'JM3' and hereinafter referred to by the name 'JM3'.

The new Crapemyrtle plant is a product of a planned breeding program conducted by the Inventor in Poplarville, Miss. The objective of the breeding program was to develop new vigorous and freely-branching Crapemyrtle plants with dark-colored leaves and attractive flower colors.

The new Crapemyrtle plant originated from a cross-pollination conducted by the Inventor during the summer of 2015 of *Lagerstroemia* x *indica* 'Ebony Flame', not patented, as the female, or seed, parent with *Lagerstroemia indica* 'Natchez White', not patented, as the male, or pollen, parent. The new Crapemyrtle plant was discovered and selected by the Inventor in May, 2016 as a single flowering plant from within the progeny of the stated cross-pollination in a controlled nursery environment in Poplarville, Miss.

Asexual reproduction of the new Crapemyrtle plant by vegetative softwood cuttings in a controlled greenhouse environment in Poplarville, Miss. since August, 2016 has shown that the unique features of the new Crapemyrtle plant are stable and reproduced true to type in successive generations of asexual reproduction.

SUMMARY OF THE INVENTION

Plants of the new Crapemyrtle have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'JM3'. These characteristics in combination distinguish 'JM3' as a new and distinct Crapemyrtle plant:

1. Upright to slightly outwardly spreading plant habit.
2. Freely branching habit.
3. Vigorous and sturdy growth habit.
4. Dark greyed purple-colored leaves.
5. Numerous inflorescences with light purple-colored flowers.
6. Good garden performance and pathogen resistance.

Plants of the new Crapemyrtle can be compared to plants of the female parent, 'Ebony Flame'. Plants of the new Crapemyrtle differ primarily from plants of 'Ebony Flame' in the following characteristics:

1. Plants of the new Crapemyrtle are larger and more vigorous than plants of 'Ebony Flame'.
2. Plants of the new Crapemyrtle have light purple-colored flowers whereas plants of 'Ebony Flame' have red-colored flowers.

Plants of the new Crapemyrtle can be compared to plants of the male parent, 'Natchez White'. Plants of the new Crapemyrtle differ primarily from plants of 'Natchez White' in the following characteristics:

1. Plants of the new Crapemyrtle are more freely branching than plants of 'Natchez White'.

2. Plants of the new Crapemyrtle have dark greyed purple-colored leaves whereas plants of 'Natchez White' have light green-colored leaves.
3. Plants of the new Crapemyrtle have light purple-colored flowers whereas plants of 'Natchez White' have white-colored flowers.

Plants of the new Crapemyrtle can be compared to plants of *Lagerstroemia indica* 'JM1', disclosed in U.S. Plant patent application Ser. No. 16/350,178. Plants of the new Crapemyrtle differ primarily from plants of 'JM1' in the following characteristics:

1. Plants of the new Crapemyrtle have dark greyed purple-colored leaves whereas plants of 'JM1' have dark green-colored leaves.
2. Plants of the new Crapemyrtle have light purple-colored flowers whereas plants of 'JM1' have dark red to dark red purple-colored flowers.

Plants of the new Crapemyrtle can be compared to plants of *Lagerstroemia indica* 'JM4', disclosed in U.S. Plant patent application Ser. No. 16/350,179. Plants of the new Crapemyrtle differ primarily from plants of 'JM4' in the following characteristics:

1. Plants of the new Crapemyrtle are taller and more vigorous than plants of 'JM4'.
2. Plants of the new Crapemyrtle have light purple-colored flowers whereas plants of 'JM4' have white-colored flowers.

Plants of the new Crapemyrtle can be compared to plants of *Lagerstroemia indica* 'JM5', disclosed in U.S. Plant patent application Ser. No. 16/350,175. Plants of the new Crapemyrtle differ primarily from plants of 'JM5' in the following characteristics:

1. Plants of the new Crapemyrtle are not as vigorous as plants of 'JM5'.
2. Plants of the new Crapemyrtle have light purple-colored flowers whereas plants of 'JM5' have light red purple-colored flowers.

Plants of the new Crapemyrtle can be compared to plants of the *Lagerstroemia indica* 'Catawba', not patented. In side-by-side comparisons, plants of the new Crapemyrtle differ primarily from plants of 'Catawba' in the following characteristics:

1. Plants of the new Crapemyrtle have dark greyed purple-colored leaves whereas plants of 'Catawba' have green-colored leaves.
2. Plants of the new Crapemyrtle have light purple-colored flowers whereas plants of 'Catawba' have dark purple-colored flowers.
3. Plants of the new Crapemyrtle are more resistant to pathogens than plants of 'Catawba'.

Plants of the new Crapemyrtle can be compared to plants of the *Lagerstroemia indica* 'Muskogee', not patented. In side-by-side comparisons, plants of the new Crapemyrtle differ primarily from plants of 'Muskogee' in the following characteristics:

1. Plants of the new Crapemyrtle have dark greyed purple-colored leaves whereas plants of 'Muskogee' have dark green-colored leaves.
2. Plants of the new Crapemyrtle have smaller inflorescences than plants of 'Muskogee'.
3. Plants of the new Crapemyrtle have light purple-colored flowers whereas plants of 'Muskogee' have purple-colored flowers.
4. Plants of the new Crapemyrtle are more resistant to pathogens than plants of 'Muskogee'.

BRIEF DESCRIPTION OF THE PHOTOGRAPHS

The accompanying colored photographs illustrate the overall appearance of the new Crapemyrtle plant showing the colors as true as it is reasonably possible to obtain in colored reproductions of this type. Colors in the photographs may differ slightly from the color values cited in the detailed botanical description which accurately describe the colors of the new Crapemyrtle plant.

The photograph on the first sheet (FIG. 1 of 2) is a side perspective view of a typical plant of 'JM3' grown in a container in an outdoor nursery.

The photograph on the second sheet (FIG. 2 of 2) is a close-up view of a typical flowering plant of 'JM3' grown in a container in an outdoor nursery.

DETAILED BOTANICAL DESCRIPTION

The aforementioned photographs and following observations, measurements and values describe plants grown in 7-gallon containers in Park Hill, Okla. and Fort Worth, Tex. during the summer in outdoor nurseries and under cultural conditions which closely approximate commercial Crapemyrtle production. During the production of the plants, day temperatures averaged 33° C. and night temperatures averaged 14° C. Plants were three years when the photographs and the description were taken. In the following description, color references are made to The Royal Horticultural Society Colour Chart, 2015 Edition, except where general terms of ordinary dictionary significance are used.

Botanical classification: *Lagerstroemia indica* 'JM3'.

Parentage:

*Female, or seed, parent.*—*Lagerstroemia indica* 'Ebony Flame', not patented.

*Male, or pollen, parent.*—*Lagerstroemia indica* 'Natchez White', not patented.

Propagation:

*Type.*—By vegetative softwood and hardwood cuttings.

*Time to initiate roots, summer.*—About ten days at temperatures about 21° C. to 33° C.

*Time to initiate roots, winter.*—About 25 days at temperatures about 21° C. to 33° C.

*Time to produce a rooted young plant, summer.*—About one month at temperatures about 21° C. to 33° C.

*Time to produce a rooted young plant, winter.*—About one month for softwood cuttings and about two months for hardwood cuttings at temperatures about 21° C. to 33° C.

*Root description.*—Medium in thickness, fibrous; typically brownish white in color, actual color is dependent on substrate composition, water quality, fertilizer type and formulation, substrate temperature and physiological age of roots.

*Rooting habit.*—Freely branching; dense.

Plant description:

*Plant form and growth habit.*—Perennial shrub; upright to slightly outwardly spreading plant habit; vigorous and sturdy growth habit.

*Branching habit.*—Freely branching habit with about four to six basal lateral branches each with numerous secondary and tertiary lateral branches developing per plant.

*Plant height*.—About 138 cm.

*Plant diameter* (*area of spread*).—About 57 cm.

Lateral branch description:

*Length*.—About 135 cm.

*Diameter, at the base*.—About 2 cm.

*Internode length*.—About 2 cm.

*Strength*.—Strong.

*Aspect*.—Erect to about 25° from vertical.

*Texture and luster*.—Smooth, glabrous; woody with age; matte.

*Color, immature*.—Close to 187A.

*Color, mature*.—Close to 177A and with subsequent development, close to 199A.

Leaf description:

*Arrangement*.—Alternate; simple.

*Length*.—About 5.4 cm.

*Width*.—About 3.2 cm.

*Shape*.—Elliptic.

*Apex*.—Acute to acuminate.

*Base*.—Cuneate.

*Margin*.—Entire, undulate.

*Texture and luster, upper and lower surfaces*.—Smooth, glabrous; slightly glossy.

*Venation pattern*.—Pinnate.

*Color*.—Developing leaves, upper surface: Close to N187A tinged with close to 187A. Developing leaves, lower surface: Close to 147A tinged with close to 187A. Fully expanded leaves, upper surface: Close to N187A tinged with close to 187A; with subsequent development, becoming closer to 200A; venation, close to 187A. Fully expanded leaves, lower surface: Close to 147A tinged with close to 187A; venation, close to 187A to 187B.

*Petioles*.—Length: About 3 mm. Diameter: About 1 mm. Texture and luster, upper and lower surfaces: Smooth, glabrous; slightly glossy. Color, upper and lower surfaces: Close to 146A to 146B.

Flower description:

*Flower type, arrangement and habit*.—Showy single ruffled flowers arranged in terminal panicles; freely flowering habit with usually about 16 flowers per inflorescence and numerous inflorescences developing during the flowering season; flowers face upright and outwardly; flowers not persistent.

*Natural flowering season*.—Plants of the new Crapemyrtle flower during the summer and into the autumn in Fort Worth, Tex.

*Fragrance*.—None detected.

*Inflorescence height*.—About 5.2 cm.

*Inflorescence diameter*.—About 4.5 cm.

*Flower diameter*.—About 2 cm.

*Flower depth*.—About 1.5 cm.

*Flower buds*.—Length: About 1 cm. Diameter: About 9 mm. Shape: Roughly spherical. Texture and luster: Smooth, glabrous; glossy. Color: Close to 146A; towards the apex, close to 187A.

*Petals*.—Quantity per flower and arrangement: Six arranged in a single whorl. Length: About 1 cm. Width: About 8 mm. Shape: Roughly orbicular. Apex: Rounded, undulate; ruffled. Base: Rounded. Margin: Entire, undulate; ruffled. Texture and luster, upper and lower surfaces: Smooth, glabrous; soft; delicate; matte. Color: When opening, upper and lower surfaces: Close to 75A. Fully opened, upper and lower surfaces: Close to 75A; color does not change with development. Stalk: Close to 67C to 67D.

*Sepals*.—Quantity per flower and arrangement: Six arranged in a single whorl. Length: About 9 mm. Width: About 4 mm. Shape: Narrowly deltoid. Apex: Acute. Base: Fused. Margin: Entire. Texture and luster, upper and lower surfaces: Smooth, glabrous; glossy. Color: When opening and fully opened, upper surface: Close to 146A to 146B. When opening and fully opened, lower surface: Close to 146A.

*Pedicels*.—Length: About 6 mm. Diameter: About 1.5 mm. Strength: Strong, flexible. Aspect: About 45° from stem axis. Texture and luster: Smooth, glabrous; matte. Color: Close to 187A.

*Reproductive organs*.—Androecium: Quantity per flower: About twelve. Filament length: About 8 mm. Filament color: Close to 58D. Anther length: About 1.25 mm. Anther shape: Oblong. Anther color: Close to 9A. Amount of pollen: None. Gynoecium: Quantity per flower: One. Pistil length: About 1 cm. Style length: About 7.5 mm. Style color: Close to 60C. Stigma appearance: Spherical. Stigma color: Close to 148A. Ovary: Close to 11B.

*Fruits and seeds*.—Fruit and seed development has not been observed on plants of the new Crapemyrtle.

Garden performance: Plants of the new Crapemyrtle have been observed to have good garden performance and to tolerate rain, wind and temperatures ranging from about −10° C. to about 38° C. and to be cold hardy to USDA Hardiness Zone 6.

Pathogen & pest resistance: Plants of the new Crapemyrtle have been observed to be resistant to leaf spot (*Cercospora lythracearum*) and powdery mildew (*Erysiphe lagerstroemia*). Plants of the new Crapemyrtle have not been observed to be resistant to pests and other pathogens common to Crapemyrtle plants.

It is claimed:

1. A new and distinct Crapemyrtle plant named 'JM3' as illustrated and described.

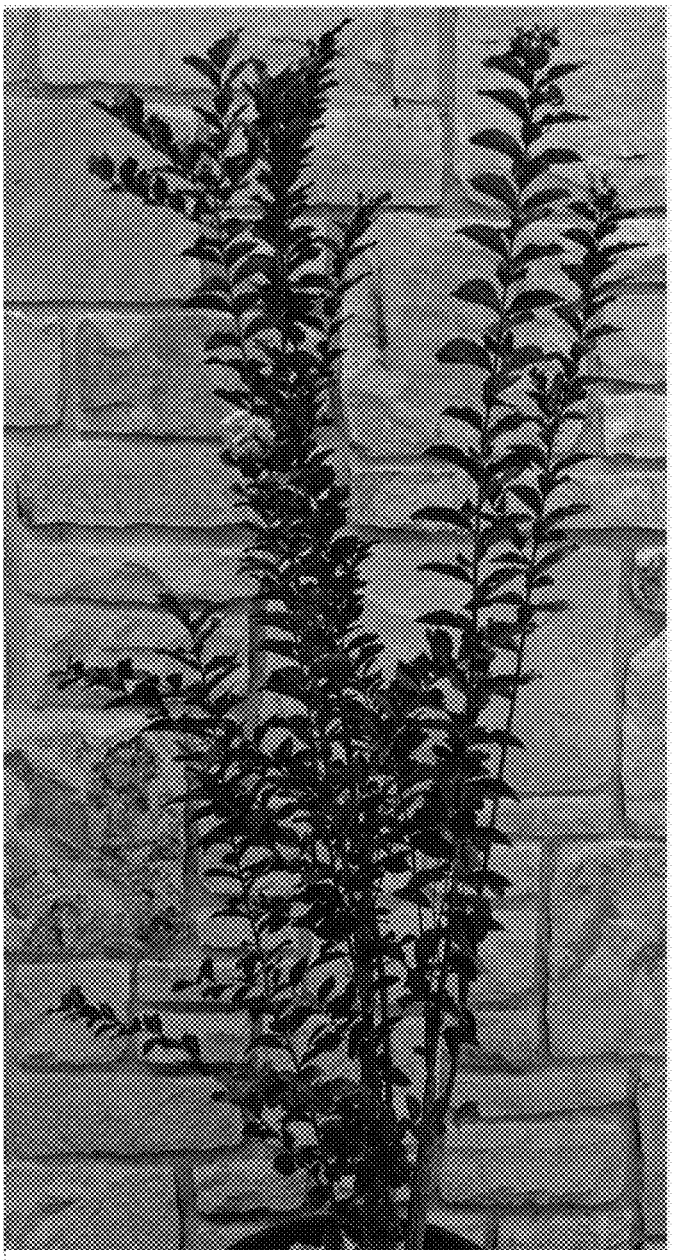

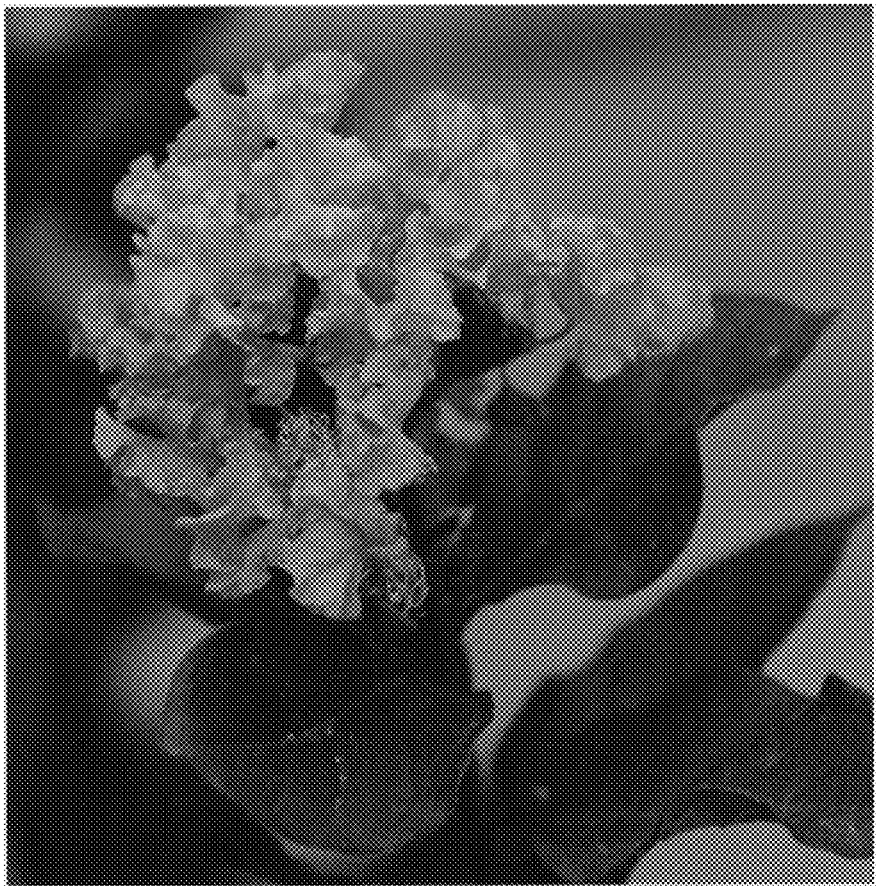

* * * * *